United States Patent
Barbucci et al.

(10) Patent No.: US 6,831,172 B1
(45) Date of Patent: Dec. 14, 2004

(54) CROSS-LINKED HYALURONIC ACIDS AND MEDICAL USES THEREOF

(75) Inventors: Rolando Barbucci, Milan (IT); Roberto Rappuoli, Milan (IT)

(73) Assignee: Farmila-Thea Farmaceutici S.p.A., Settimo Milanese (IT)

(*) Notice: Subject to any disclaimer, the term of this patent is extended or adjusted under 35 U.S.C. 154(b) by 0 days.

(21) Appl. No.: 09/830,761

(22) PCT Filed: Nov. 8, 1999

(86) PCT No.: PCT/EP99/08481

§ 371 (c)(1),
(2), (4) Date: Jun. 18, 2001

(87) PCT Pub. No.: WO00/27887

PCT Pub. Date: May 18, 2000

(30) Foreign Application Priority Data

Nov. 11, 1998 (IT) .......................................... MI98A2440

(51) Int. Cl.[7] .......................... C07H 13/02; C07H 5/06; C07H 1/00; A61K 31/715

(52) U.S. Cl. ..................... 536/53; 536/123.13; 536/124; 514/53; 514/54

(58) Field of Search ............................... 536/53, 123.1, 536/124; 514/53, 54

(56) References Cited

U.S. PATENT DOCUMENTS 5,616,568 A * 4/1997 Pouyani et al. ................ 514/54
5,874,417 A * 2/1999 Prestwich et al. ............. 514/54
5,944,753 A * 8/1999 Galin et al. ..................... 632/6

* cited by examiner

Primary Examiner—James O. Wilson
Assistant Examiner—Everett White
(74) Attorney, Agent, or Firm—Walter H. Schneider

(57) ABSTRACT

Cross-linked hyaluronic acids produced by the reaction of the carboxylic acid groups of hyaluronic acid and a polyamine and the sulfated and hemisuccinylated derivates thereof. The cross-linked hyaluronic acids are useful for various pharmaceutical and medical purposes.

3 Claims, No Drawings

CROSS-LINKED HYALURONIC ACIDS AND MEDICAL USES THEREOF

FIELD OF THE INVENTION

The present invention concerns cross-linked hyaluronic acids, optionally hemisuccinylated or sulphated, the salts thereof with biologically suitable or pharmacologically active cations and the complexes thereof with heavy metals such as copper, zinc and iron.

The invention also concerns the use of said cross-linked hyaluronic acids, salts and complexes in the medical, pharmaceutical and cosmetic fields.

BACKGROUND OF THE INVENTION

Hyaluronic acid is a glycosaminoglycan consisting of disaccharide units of D-glucuronic acid and N-acetylglucosamino-2-acetamido-2-deoxy-D-glucose, connected by β (1→3) glycoside bonds.

Natural hyaluronic acid has linear, not cross-linked structure of molecular weight ranging from 50,000 to 8,000,000 D or more, depending on the source and extraction method.

Hyaluronic acid is present in the synovial liquid, connective tissue and vitreous humor of higher animals, as well as in some bacteria.

Compositions of sodium hyaluronate having various molecular weights (in the form of solutions having different viscosities, gels with different viscoelastic characteristics, sponges, films or membranes) are used in human medicine and surgery for instance as substitutes of synovial liquid, tissular antiadhesive agents, substitutes of vitreous humor, artificial tears, agents for the in vivo tissular re-constitution (for instance as extra-cellular matrices for the formation of bone segments, following the colonisation of osteoblasts and subsequent calcification; of connective-dermal tissues, following the colonisation of fibroblasts), materials for the preparation of artificial skin useful in the treatment of burns or in plastic surgery; coating agents for biocompatible vascular prosthesis, carriers of pharmacologically by active ingredients in controlled-release formulations, etc.

In dermatology and cosmetology, in view of the viscoelastic and moisturising properties and of the high biocompatibility, said compositions are used both as bases for moisturising topical formulations and as invasive medical-surgical devices ("filling agents").

The use of natural, linear hyaluronic acid for said uses is however limited by its in vivo fast degradation by enzymatic systems such as hyaluronidase, glucosidase and glucuronidase, with subsequent decrease in the molecular weight and progressive impairment of the viscoelastic properties and, generally, of the physical characteristics of the final compositions and devices (mechanical strength, elasticity, pore size,) etc.

In order to overcome this problem, mainly with the purpose of increasing the range of compositions and their applicative flexibility, chemically modified hyaluronic acids have been proposed.

Cross-linking with polyfunctional epoxides (U.S. Pat. Nos. 4,716,224, 4,772,419, 4,716,154), polyalcohols (U.S. Pat. No. 4,957,744), divinylsulphone (U.S. Pat. Nos. 4,582,865, 4,605,601, 4,636,524), aldehydes (U.S. Pat. Nos. 4,713,448, 5,128,326, 4,582,568), biscarbodiimides (U.S. Pat. No. 5,356,883), polycarboxylic acids (EP-A-718312) has been disclosed.

Said cross-linked hyaluronic acids are used as biomaterials for implants, prosthesis and medical devices, as controlled-release matrices for medicaments, as healing, anti-adhesive and dressing agents.

The sulphation of non cross-linked hyaluronic acid is generally disclosed in U.S. Pat. No. 5,013,724, mainly concerning the sulphation of heparines, heparans and dermatans for use as antithrombotic and anti-coagulant agents.

The hemisuccinylation recreation of hyaluronic acid (HY) has never been disclosed. An example of this functionalization is disclosed in EP-B-200574, claiming composite biomaterials consisting of succinylated collagen and chitosan.

The cross-linking of carboxyalkyl cellulose by means of di- or polyamines is disclosed in EP-A-566118 (Kimberly Clark Corp) for the preparation of absorbing materials with HY as cross-linking agent, by heating. Such a method appears to be economically advantageous and suitable for the large-scale productions required for this kind of products.

EP-A-462 426 (Fidia) discloses perforated biocompatible membranes and their uses as artificial skin. Collagen cross-linked with diamines and hyaluronic acid are generically cited as possible materials for said membranes.

SUMMARY OF THE INVENTION

It has now been found that new cross-linked hyaluronic acids obtainable by reaction of suitably activated carboxy groups of HY with a polyamine, as well as the salts and complexes with suitable organic or inorganic cations, have advantageous chemico-physical and biological properties for the biomedical and cosmetic uses.

The main chemico-physical and biochemical characteristics of the compounds of the invention are:

high biocompatibility;

high resistance to enzymatic degradation mainly after sulphation;

high capacity to adsorb water, with formation of viscoelastic characteristics dependent on the cross-linking degree as well as on sulphation and/or hemi-succinylation degree;

ability to chelate metal ions such as zinc or copper; said derivatives having very good stability.

The biological behaviour is new and surprising; it is known that sulphation (or supersulphation) of glycosaminoglycans such as heparin, dermatan sulphate, chondroitin and native hyaluronic acid is known to increase their anti-coagulant properties (inhibition of Xa and IIa factors and/or change of their ratio) with respect to the starting product (U.S. Pat. No. 5,013,724).

The compounds of the invention, when sulphated, have a slight anticoagulant activity, whereas it is completely surprising the lack of platelet activation and aggregation (measured as antiadhesive activity; P.R.P. model in rabbits subjected to behavioural stress, described in "Abstract IL 15"—International Conference on Advances in Biomaterials and Tissue Engineering, 14–19 Juin 1998, Capri Italy) both for the cross-linked hyaluronic acid of the invention (with different cross-linking degrees) and for the corresponding sulphate esters; this property is totally absent in the natural hyaluronic acid and esther derivatives.

No polymeric materials for medical use up to now known apparently shares the same property.

DETAILED DISCLOSURE OF THE INVENTION

The invention concerns new cross-linked hyaluronic acids obtainable by reaction of activated carboxylic groups of native linear hyaluronic acid, of extractive or biosynthetic route, with a polyamine, particularly a linear alkyl diamine.

According to a preferred embodiment, the cross-linked hyaluronic acid of the invention is further subjected to sulphation and hemi-succinylation processes. The obtained products and their salts or complexes have entirely new properties (for instance, swelling, water motility within the gel; chemotactic activity on endothelial cells, viscoelastic properties).

Said esterification processes are carried out by known methods (use of reagents pyridine/$SO_3$; chlorosulphonic acid; succinic anhydride, in homogeneous or heterogeneous phase, at pH from 6.5 to 8).

Examples of the hemisuccinylation process for collagen are reported in WO 88/10123 and in U.S. Pat. No. 4,493,829.

The polyamine to be used as cross-linking agent according to the invention is preferably a diamine of formula $R_1NH-A-NHR_2$ wherein A is a $C_2-C_{10}$ linear or branched alkylene chain, preferably a $C_2-C_6$ chain, optional substituted by hydroxy, carboxy, halogen, alkoxy and amino groups; a polyoxyalkylene chain $[(CH_2)_n-O-(CH_2)_n]_m$ wherein n is 2 or 3, m is an integer from 2 to 10; a $C_5-C_7$ cycloalkyl group; an aryl or hetaryl group, preferably 1, 4 or 1, 3 disubstituted benzene; $R_1$ and $R_2$, which are the same or different, are hydrogen, $C_1-C_6$ alkyl, phenyl or benzyl groups.

Preferred meanings of A are $C_2-C_6$ alkylene or a chain $[(CH_2), -O-(CH_2)_n]_m$. $R_1$ and $R_2$ are preferably hydrogen.

The polyamine is reacted with hyaluronic acid or salts thereof, the carboxylic groups of which have been previously activated.

The activation may be carried out with conventional methods; for instance, and preferably, those commonly used, in anhydrous aprotic solvent, to form amide bonds in peptide synthesis such as carbonyldiimidazole; carbonyl-triazole; hydroxybenzotriazole; N-hydroxysuccinimide; p-nitrophenol+p-nitrophenyltrifluoro acetate, chloromethylpyridylium iodide; preferably chloromethypyridylium iodide and like; these activators allow the best yields and the highest reproducibility in terms of cross-linking degree.

The hyaluronic acid is preferably salified with a lipophilic cation, for instance tetralkylammonium or other lipophilic organic bases able to induce the suitable solubility in the polar aprotic solvent such as dimethylformamide, tetrahydrofuran or the like.

The transformation of inorganic salts such as sodium into suitable organic cations may be carried out by well known ion-exchange methods in homogeneous phase or by precipitation of the acid component, its recovery and subsequent salification with the desired organic base.

The activation reaction of the carboxy groups is usually carried out in homogeneous phase and in anhydrous polar aprotic solvent.

The cross-linking polyamine is added to the solution of the activated ester in the same anhydrous solvent, keeping the temperature from 0 to 30° C. The reaction times range from 1 to 12 hours, depending on the presence of suitable bases such as triethylamine.

In general, the desired final product is recovered by addition of a different solvent under reduced pressure, followed by conventional work-up.

The cross-linking degree may be comprised within wide limits and may be adjusted by changing the amount of the carboxy-activating agent, the activation and the cross-linking reactions being practically quantitative.

As a consequence, the desired cross-linking degree (C.L.D.: percent of carboxylic groups involved in the cross-linking) is perfectly reproducible, as shown by the N.M.R. data. The final products obtained under similar operative conditions have therefore constant characteristics.

The starting hyaluronic acid may be any hyaluronic acid having molecular weight from about 5,000 to 8,000,000 D, preferably from 10,000 to 200,000 D, extracted from conventional sources or obtainable by fermentation of microorganisms of the group *Streptococcus* or other engineered strains.

The cross-linked hyaluronic acid of the invention may be subjected to sulphation reaction with a suitable reagent, preferably the pyridine/sulphur trioxide complex in dimethylformamide.

The reaction is carried out in heterogeneous phase at a temperature of 0–10° C. for reaction times ranging from about 0,5 to about 6 hours.

The obtainable sulphation degree may be comprised within wide limits and may be adjusted by changing the reaction time and the temperature.

Generally, the sulphation degree (defined as eq. Sulphate groups/g) may range from $1 \times 10^{-6}$ to $6 \times 10^{-6}$, preferably about $2 \times 10^{-6}$ eq./g for a C.L.D. =0.5.

The cross-linked hyaluronic acid of the invention may also be subjected to hemisuccinylation reactions in known conditions (aqueous heterogeneous phase, under strong stirring, addition of solid succinic anhydride in subsequent portions, in ratios from 1:1 to 1:5 by weight; keeping the pH from 7 to 8.5 with alkali, at temperatures ranging from 5 to 30° C.). The hemisuccinylation degree may be comprised within wide limits depending on the following parameters: reaction time and temperature; stirring speed of the polyphasic system and addition rate of solid succinic anhydride. By keeping said parameters constant, the reaction gives reproducible products. The cross-linked hyaluronic acids, optionally sulphated or hemisuccinylated, of the invention show the ability to form complexes with metal ions such as copper, zinc, iron.

These complexes may be easily obtained by dissolving or by dispersing until complete swelling the hyaluronic acid derivative in water and adding under stirring preferably at room temperature, a concentrated solution of an organic or inorganic salt of copper, zinc or iron, for instance $CuCl_2$, $ZnCl_2$, or $Fe_2(SO_4)_3$; after 12–24 hours under stirring, the complex is recovered by centrifugation or precipitation following change of solvent (e.g. addition of ethanol or acetone) or evaporation under reduced pressure; the recovered crude product is thoroughly washed with distilled water so as to remove the excess ion.

The complexes are then freeze-dried.

The content of metal ions depends on the used operative conditions: polymer to ion molar ratios, concentration and pH of the solution; reaction times and particularly the cross-linking degree. It may reach the maximum volume of 1 metal ion per disaccharide unit not involved in the cross-linking.

An important advantage of the invention consists in the possibility of obtaining, by suitably changing the cross-linking degree and/or the sulphation or succinylation degree, hyaluronic acid derivatives in a wide range of different forms, characterised by different properties (such as viscoelasticity, metal ions, ability to form hydrogels, films, sponges, mechanical strength etc.).

This allows the use of the hyaluronic acid derivatives of the invention in several medical and pharmaceutical fields, in the human or veterinary field:

1) as intraarticular substitutes of the synovial liquid for the treatment of osteoarthritic conditions;
2) as vitreous humor substitutes for the treatment of pathologies and side-effects connected to ophthalmic surgery;
3) as base of artificial tears formulation, suited for the therapy of dry eye;
4) as controlled—release matrices of medicaments (e.g. antiinflammatories, antibiotics, β-adrenergic agonists and antagonists, aldose reductase inhibitors, anti-acne, antiallergic, anti-alopecia, antineoplastic, antiglaucoma, anti-itching, anti-psoriasis, antiseborrhea, anti-ulcer, antiviral agents, growth factors etc.) by simple inclusion into the hydrogels obtained from the compounds of the invention. Alternatively to the in inclusion process, the medicament may be bound by covalent bonds to the hyaluronic acid matrices, by means of:
  a) esterification or amidation of COOH not involved in the cross-linking with polyamines, when the medicament is an alcohol or an amine;
  b) esterification with the free hydroxy groups of hyaluronic acid derivatives when the medicament has free carboxy groups.

The products under a) may be obtained using the same activation method of the carboxy groups described above in a carefully anhydrous medium or by transesterification.

5) For the preparation of device for wound or skin ulcers healing in form of films of different thickness, more or less permeable to gases, sponges etc. Said devices preferably contain suitable drugs such as antibiotics, healing factors. They are also useful in the culture of epithelial cells, keratinocytes etc.;
6) For all the applications for which the use of known hyaluronic acids has already been proposed, for instance the preparation of solid or semi-solid forms or moldable form for the production of vascular prosthesis (antiadhesive dressings of blood vessels, artificial heart valves etc.); of biohybrid organs (artificial pancreas, liver); of ophthalmic products (lens substitutes, contact lens); of otological products; generally of anti-adhesive implants, to be used in abdominal, gynaecological, plastic, orthopaedic, neurological, ophthalmological, thoracic, otorhinolaryngological surgery; of medical device such as stents, catheters, cannulas and the like.

The uses of cross-linked hyaluronic acid and of biomaterials obtained therefrom are known and described, for instance, in WO 97/39788, WO 97/22629, WO 97/18244, WO 97/7833, EP 763754, EP 718312, WO 96/40005, WO 96/33751, U.S. Pat. No. 5,532,221, WO 95/1165 e EP 320164.

The use of the cross-linked hyaluronic acids of the invention in cosmetic dermatology is of particular interest, for instance as moisturizing agents, bases of various cosmetological formulations, injectable filling agents etc.

The formal products obtained from the cross-linked hyaluronic acid derivatives of the invention may by subjected to sterilisation processes (for instance by heating to 120° C. or by means of ethylene oxide) without any change in the technological properties, which is of course a further advantage provided by the present invention.

The present invention is described in more detail in the following examples.

EXAMPLE 1

Hyaluronic acid sodium salt ($1 \times 10^{-3}$ mol., with reference to the disaccharidic unit) were transformed in TBA salt, according to one of the following methods:

a) 1% aqueous solution of sodium hyaluronate is transformed in $H^+$ form by $H^+$ cationic strong resin (Amberlite IR 120); the final solution is treated by a 0,5% solution of TBA-OH to about pH=9.

b) 1% aqueous solution of sodium hyaluronate is transformed in TBA salt solution by treating with a cationic weak resin in $TBA^{30}$ form. (Amberlite IRC 50)

In both cases, the final solutions are liophylised. The TBA salt is then dissolved in 15 ml of anhydrous DMF, under $N_2$, and—at 0° C.—0, 02 g of cloronethypyridylium Iodide (CMPJ) in 2 ml of anhydrous DFM, are added dropwise to the stored solution of TBA.salt.

The reaction mixture was then added with 0.1 ml of triethylamine and, then, dropwise, with a solution of 1,3-diaminopropane (d=0.88, in large excess, so as to make cross-linking of the activated carboxy groups easier) in 2 ml of anhydrous DMF. When the addition was over, the reaction mixture was stirred for at least 30' and the solvent was then removed under reduced pressure, the residue was then taken up with DMF, which was subsequently removed by distillation; the residue was then treated with ethanol, ethanol-water and finally with water.

The product was then lyophilised and the residue subjected to analysis.

I.R. (film): 1630 $cm^{-1}$ (—CO—NH); 1740 $cm^{-1}$ (—COOH, polysaccharide); 3200 $cm^{-1}$ (—NH—).

SD (Swelling Degree, in water and r.t., after 15'; gravimetric determination; calculated according to:

$$SD = \frac{W_s - Wd}{Wd} \cdot 100,$$

where:

$W_s$=weight of hydrated gel; Wd=weight of dry gel): 31.000

Cross-linking degree: 0.05 (5% of initially available carboxy groups).

EXAMPLE 2

According to the procedure and conditions reported in example 1, using the same HY and the same activating agent but 1,6-diaminohexane instead of 1,3-diaminopropane, a cross-linked hyaluronic acid having cross-linking degree of 0.05 was obtained.

I.R. (film): 1630 $cm^{-1}$ (—CO—NH); 1740 $cm^{-1}$ (—COOH polysaccharide); 3200 $cm^{-1}$ (—NH—).

EXAMPLE 3

According to the procedure and conditions used in example 1, using as a cross-linking agent 0,0'-dis-(2-aminopropyl) PEG 500, a hyaluronic acid having a cross-linking degree of 0.05 was obtained.

I.R. (film): 1630 $cm^{+1}$ (—CO—NH); 1740 $cm^{-1}$ (—COOH polysaccharide); 3200 $cm^{-1}$ (—NH—).

SD=31.000

EXAMPLE 4

0.6 g of hyaluronic acid tributylammonium salt ($1 \times 10^3$ mol., with reference to the disaccharide unit) were dissolved under stirring in 30 ml of DMF under nitrogen. 0.08 g of chloromethylpyridylium iodide ($3.5 \times 10^{-4}$ mol) dissolved in 2 ml of DMF were added dropwise to the stirred solution kept at 0° C. The molar ratio was therefore about 3/1.

After 20 minutes 2 ml of 1,3-diaminopropane (0.024 mol) were added, followed immediately by 0.5 ml of triethylamine. A solid, gelatinous product was obtained, the product was then swelled with water and washed again with ethanol.

The final product, after lyophilisation, shows at the scanning microscope an irregular pattern with smooth zones alternating to spongy zones.

The cross-linking degree was 0.3 (30% of initially available carboxy groups)

I.R. (film): 1740 cm$^{-1}$ (—COOH); 1630 cm$^{-1}$ (—CO—NH); 1610 cm$^{-1}$ (—COO—); 1560 cm$^{-1}$ (—CO—NH—)

EXAMPLE 5

0.6 g of hyaluronic acid tributylammonium salt (HY TBA) (1×10$^{-3}$ mol., with reference to the disaccharide unit) were dissolved under stirring in 30 ml of DMF under nitrogen. 0.15 g of chloromethylpyridylium iodide (CMPJ) (6×10$^{-6}$ mol) dissolved in 2 ml of DMF were added dropwise to the solution, kept at 0° C. The molar ratio was 2HY.TBA:1 CMPJ. After 20 minutes, 2 ml of 1,3 diaminopropane (0.024 mol.) were added to the solution.

0.5 ml of triethylamine were added thereafter.

A solid, gelly-like product was obtained and thoroughly washed with DMF.

After evaporating DMF, the product was swelled in water and washed with ethanol before lyophilization.

The obtained product had a cross-linking degree of 0.5 and showed at the scanning microscope a grainy aspect interspaced by large meshes. At higher magnitudes, the two morphologies appear identical and show round-shaped protrusions a few microns in diameter.

IR (film): 1740 cm$^{-1}$ (—COOH); 1630 cm$^{-1}$ (—CO—NH—); 1610 cm$^{-1}$ (—COO); 1560 cm$^{-1}$ (—CO—NH—);

The gels were subjected to swelling in PBS and the max swelling ability was evaluated.

SD=23.500
NMR=(13 C; ppm): 29.3 and 39.8

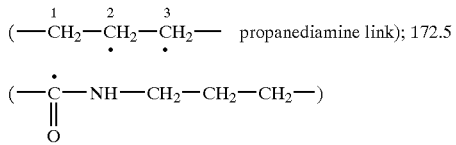

The rheological properties evaluated on Bohlin VOR Rheometer, at the temperature of 23±0.1° C., show that the dynamic elastic module G' (100 Pa at 10 Hz) identical at the two considered concentrations (10 and 20 mg/ml) is always higher than the viscous dynamic module (G" 40 Pa for 20 mg at 10 Hz and 20 Pa for 10 mg at 10 Hz).

EXAMPLES 6–9

According to the methods disclosed in the previous examples, the cross-linked hyaluronic acid derivatives having the characteristics summarised in the following table 1, were obtained, starting from 1×10$^{-3}$ mol (0.6 g) of hyaluronic acid tributylammonium salt.

The obtained derivatives had the following properties

TABLE 1

| Ex | Cross-linking agent (mol) | Amount (g) of CMPJ (mol) | Cross-linking degree | SD | NMR (13) (ppm) | I.R. (film) (cm$^{-1}$) | Aspect at the scanning microscope |
|---|---|---|---|---|---|---|---|
| 6 | 1,3-propane-diamine (0.024) | 0.6 g (1.2 10$^{-3}$) | (100%) | 13.200 | 29.3/39.8 (—CH$_2$—CH$_2$—CH$_2$— propanediamine link); 172.5 (—C(=O)—NH—CH$_2$—CH$_2$—CH$_2$—) | 1630 (—<u>CO</u>—NH—); 1560 (—CO—<u>NH</u>—); | Homogeneouns, ondulated morphology. |
| 7 | 0,0'-1-bis-(2-diaminopropyl) PEG 500 (0.022) | 0.15 g (6 × 10$^{-4}$) | (50%) | 9.000 | | | Alternating smooth areas and meshes, circular protrusions a few microns in size. |
| 8 | 0,0'-bis(2-aminopropyl) - PEG 800 (0.022) | 0.15 g (6 × 10$^{-4}$) | (50%) | 6.100 | | | Two morphologically different zones, a first one ondulated and a second with hole-like structures. |
| 9 | 1,6-diamino-hexane (0.023) | 0.15 g (6 × 10$^{-4}$) | (50%) | 8.000 | 169.46 (—CO—NH— of cross-linking); 74.04/76.80/83.17/80.41 (—CH2— of cross-linking arm) | 1740 (—<u>CO</u>OH); 1630 (—<u>CO</u>—NH—); 1610 (—<u>CO</u>O$^-$); 1560 (—CO—<u>NH</u>—); | Smooth surface with protrusions having a few microns in size. |

EXAMPLE 10

Sulphation of 50% Cross-Linked HY

The derivative obtained in example 5 was dispersed in 5 ml DMF under strong stirring and nitrogen atmosphere.

A solution of 1 g of SO$_3$/pyridine in mol of DMF was added at 0° C. and stirred for 3 hours. The reaction was blocked by adding an excess of H$_2$O (50 ml) and the pH adjusted to 9 with 0.1M NaOH.

The product was thoroughly washed with ethanol and H$_2$O and then lyophilized.

The IR spectrum shows, in addition to the bands of the starting product, a peak at 1260 cm$^{-1}$ and a stronger band at 1025 cm$^{-1}$.

The gel swells in PBS with SD=33.000. Higher resolution 13C NMR spectrum shows the signals in H$_2$O at 37° C. reported in table 2. The intensity of the NMR signals at 29.3 and 38.8 ppm (—CH$_2$—) and the signal at 172.5 ppm (CONH) confirm a cross-linking degree of about 50%.

The rheological properties are characterised by dynamic elastic modules G' (2500 Pa with 20 mg and 1000 Pa with 10 mg at 10 Hz) which are always higher than the dynamic viscous modules G" (600 Pa with 20 mg and 150 Pa with 10 mg at 10 Hz) and much higher than the corresponding values obtained with non-sulphated HY (13 at 50%—example 5). This compound has a thrombin time (TT) higher (61±5") than the control (14.0") and the corresponding not cross-linked (14.6").

The compound was also active in the PRP test using stressed rabbit.

TABLE 2

Table: 13C Chemical shift

| C-1 | C-2 | C-3 | C-4 | C-5 | x-C=O | y-CH$_3$ | |
|---|---|---|---|---|---|---|---|
| 103.5 | 57.3 | 85.4 | 71.3 | 78.7 | 178.0 | 25.3 | ppm |
| C-1' | C-2' | C-3' | C-4' | C-5' | 6-C=O | | |
| 105.9 | 75.2 | 76.4 | 82.8 | 78.6 | 176.2 | | ppm |
| 1-CH2 | 2-CH2 | 3-CH2 | 6'-C=O | CROSS- LINKING | | | |
| 39.8 | 29.3 | 39.8 | 172.5 | | | | ppm |

EXAMPLE 11

Using the same methodology, the sulphated derivatives of 50% cross-linked products according to example 7,8, and 9, have been synthetized.

Colorimetric characteristics of the sulphated derivatives are reported in table 3 together with that of the products deriving from examples 5 and 10.

TABLE 3

| CROSSLINKED POLYMER (50% CROSS.LINKING DEGREE) | ΔHa [J/g] | Tg [° C.] | ΔHb [J/g] | Wt % water |
|---|---|---|---|---|
| C.L.Hyal-1,3 (Ex. 5) | 276 | 51 | 42 | 12 |
| C.L.HyalS-1,3 (Ex. 10) | 357 | 64 | 53 | 16 |
| C.L.Hyal-1,6 (Ex. 9) | 327 | 64 | 58 | 16 |
| C.L.HyalS-1,6 | 465 | 64 | 65 | 20 |
| 5 C.L.Hyal-P500.2NH$_2$ (Ex. 7) | 239 | 45 | 72 | 10 |
| 6 C.L.HyalS-P500.2NH$_2$ | 384 | 69 | 113 | 16 |
| 7 C.L.Hyal-P800.2NH$_2$ (Ex. 8) | 179 | 73 | 30 | 10 |

TABLE 3-continued

| CROSSLINKED POLYMER (50% CROSS.LINKING DEGREE) | ΔHa [J/g] | Tg [° C.] | ΔHb [J/g] | Wt % water |
|---|---|---|---|---|
| 8 C.L.HyalS-P800.2NH$_2$ | 206 | 76 | 52 | 10 |
| Hyal ITBA | 164 | — | 130 | 5 |

ΔHa [J/g]: water vaporization henthalpy
Tg [° C.]: enthalpy for thermal degradation process
ΔHb [J/g]: glass transition temperate
Wt % water: % of water content, based on ΔHa

EXAMPLE 12

Preparation of Complexes of Cu, Zn and Fe 100 mg of lyophilized gel of the example 5 were added, under stirring and at room temperature, to 200 ml of a concentrated solution of copper (II) chloride in distilled water. The suspension was stirred for 24 hours, and the complex was precipitated by addition of ethanol. After centrifugation, the residue was washed repeatedly with water and ethanol to remove the excess ions.

The final gel, blue-green in color, was lyophilized and analyzed.

The same procedure was carried out using ZnCl$_2$ and FeCl$_2$.

The analysis (EDAX, polarography, HCl 0.1 N titration, atomic adsorption) shows a copper content of 0.5 mol/disaccharide units.

What is claimed is:

1. A hyaluronic acid derivative comprising cross-linked molecules of hyaluronic acid obtained by the reaction of the carboxylic acid groups of a hyaluronic acid wherein the cross-linkage occurs only through amide bonds between carboxy groups of the hyaluronic acid and the amino groups of a diamine of the formula NH$_2$-A-NH$_2$ wherein A is a linear unsubstituted C$_2$–C$_6$ chain or a polyoxyalkylene chain of the formula [(CH$_2$—O—CH$_2$)$_2$]$_m$ wherein m is an interger from 2–10.

2. A cross-linked hyaluronic acid derivative according to claim 1 wherein the hydroxy groups of said hyaluronic acid derivative are sulphated or hemisuccinylated.

3. A pharmaceutical composition useful as (a) a substitute for synovial fluid in the treatment, in which the principal active ingredient is a cross-linked hyaluronic acid derivative according to claim 1.

* * * * *